(12) United States Patent
Bishop et al.

(10) Patent No.: US 7,288,655 B2
(45) Date of Patent: Oct. 30, 2007

(54) α V INTEGRIN RECEPTOR ANTAGONISTS

(75) Inventors: Brian Christopher Bishop, Hoddesdon (GB); Karel Marie Joseph Brands, Rahway, NJ (US); Ian Frank Cottrell, Hoddesdon (GB); Cameron John Cowden, Hoddesdon (GB); Antony John Davies, Hoddesdon (GB); Stephen Philip Keen, Hoddesdon (GB); David Ross Lieberman, Hoddesdon (GB); Gavin William Stewart, Hoddesdon (GB)

(73) Assignees: Merck & Co., Inc., Rahway, NJ (US); Merck Sharp & Dohme Ltd., Hoddesdon (GB)

( * ) Notice: Subject to any disclaimer, the term of this patent is extended or adjusted under 35 U.S.C. 154(b) by 51 days.

(21) Appl. No.: 10/547,407

(22) PCT Filed: Mar. 4, 2004

(86) PCT No.: PCT/GB2004/000927

§ 371 (c)(1),
(2), (4) Date: Aug. 30, 2005

(87) PCT Pub. No.: WO2004/078109

PCT Pub. Date: Sep. 16, 2004

(65) Prior Publication Data

US 2006/0149069 A1 Jul. 6, 2006

(30) Foreign Application Priority Data

| Mar. 7, 2003 | (GB) | ............................. 0305277.6 |
| Mar. 7, 2003 | (GB) | ............................. 0305278.4 |
| Mar. 7, 2003 | (GB) | ............................. 0305284.2 |

(51) Int. Cl.
*C07D 471/02* (2006.01)
*C07D 487/00* (2006.01)
*C07D 498/00* (2006.01)
*C07D 513/00* (2006.01)
*C07D 515/00* (2006.01)

(52) U.S. Cl. ..................................... 546/122; 540/580
(58) Field of Classification Search ................ 546/122; 540/580

See application file for complete search history.

(56) References Cited

U.S. PATENT DOCUMENTS 6,410,526 B1 6/2002 Duggan et al.

OTHER PUBLICATIONS

Davies et al., Tetrahedron Letters, 2004, "An efficient one-pot synthesis of annulated pyridines utilising a directed ortho-metallation/transmetallation approach", vol. 45, pp. 1721-1724.*
Reed J.N. et al, "Synthesis of 1,2,3,4-Tetrahydroquinolines and 1,2,3,4-Tetrahydro-1,6-Naphthyridines by a Directed Lithiation Reaction 1", Tetrahedron Letters, vol. 29, No. 45, pp. 5725-5728, 1988.

* cited by examiner

*Primary Examiner*—Margaret D. Seaman
*Assistant Examiner*—Niloofar Rahmani
(74) *Attorney, Agent, or Firm*—Nicole M. Beeler; David A. Muthard

(57) ABSTRACT

The present invention relates to the synthesis of intermediates for the preparation of compounds of formula (A): wherein n is 2 or 3 and various salt forms of these compounds. The compounds of formula (A) are useful as αvβ3 receptor antagonists

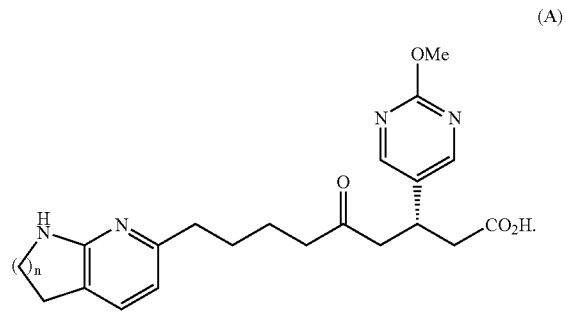

(A)

10 Claims, 4 Drawing Sheets

α V INTEGRIN RECEPTOR ANTAGONISTS

FIELD OF THE INVENTION

The present invention relates to chemical compounds, their use as intermediates in the preparation of pharmaceutical agents, and to processes for their preparation.

BACKGROUND OF THE INVENTION

International Patent Publication No. WO 00/72801 discloses a series of 3-substituted nonanoic acid derivatives of use as αvβ3 receptor antagonists, including compounds of the formula (A):

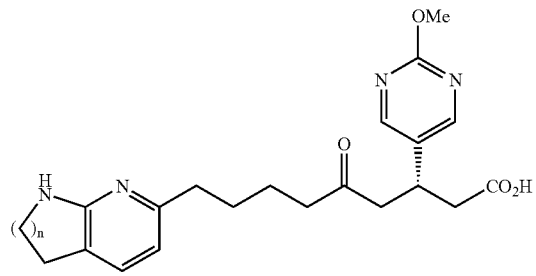

(A)

wherein n is 2 or 3.

The synthetic methods given in that application work well on a small scale, but the process is linear and requires a chiral HPLC separation of enantiomers of a penultimate intermediate. The δ-keto-acid moiety within the compound of formula (A) contains the only stereogenic carbon. There is therefore a need for an enantioselective and more efficient synthetic route to the compound of formula (A).

DETAILED DESCRIPTION OF THE INVENTION

Figure 1:
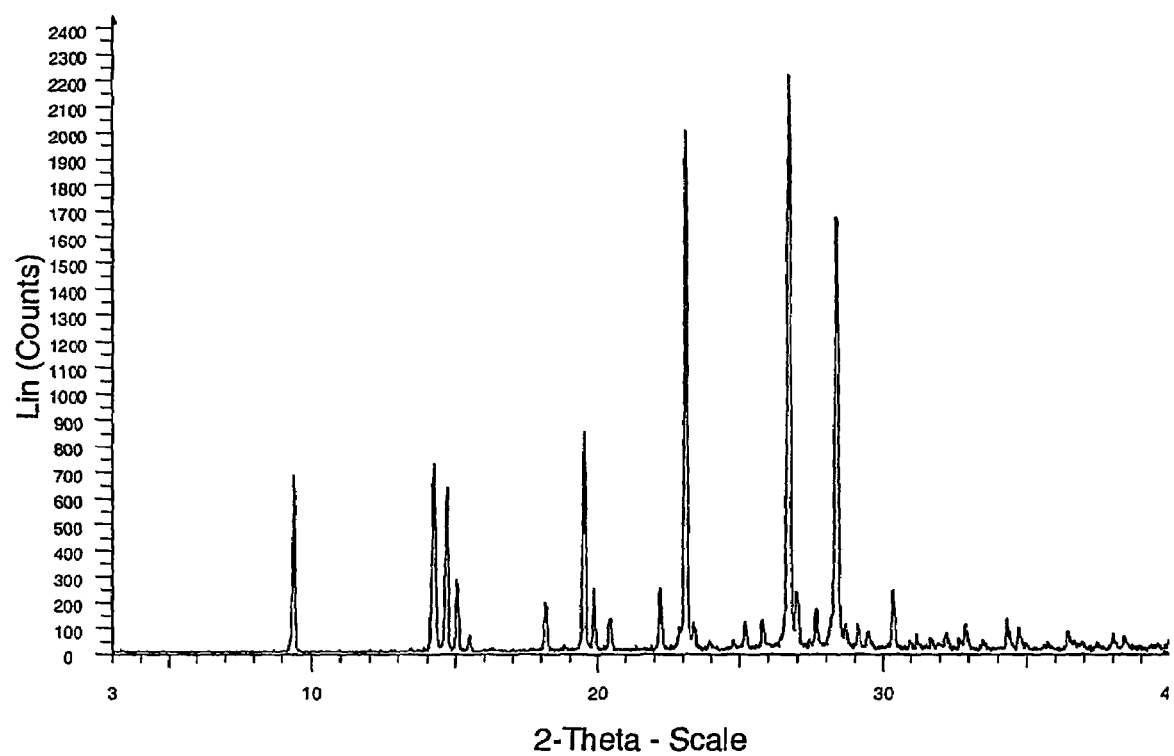
FIG. 1 is an x-ray powder diffraction (XRPD) pattern for the Form A polymorph of the product of Example 5 containing all observed XRPD reflections between 3° and 40° 2-theta. The ordinate or Y-axis is x-ray intensity (counts) and the abscissa or X-axis is the angle two-theta (2θ) in degrees.

The present invention provides compounds of general formula (I):

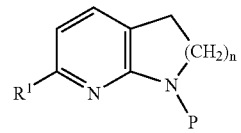

(I)

wherein n is 2 or 3, P is an amino protecting group and $R^1$ is hydrogen, chlorine, bromine or $C_1$ to $C_6$ straight or branched alkyl, are useful intermediates.

The present invention also provides a method of preparing a compound of formula (I) which comprises the ring closure of a compound of the formula (II):

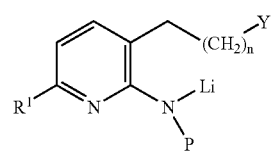

(II)

wherein $R^1$, P and n are as defined in relation to formula (I) and Y is a chlorine, bromine or iodine atom or a mesylate, tosylate, brosylate, nosylate or triflate group.

Preferably this reaction is carried out in the presence of a copper catalyst such as CuCl, CuBr, CuBr.Me$_2$S, CuI, and the like.

The compounds of formula (II) may be prepared by the reaction of a compound of the formula (III):

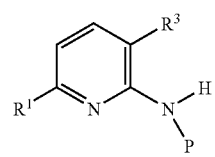

(III)

wherein $R^1$ and P are as defined in relation to formula (II) and $R^3$ is hydrogen or methyl with a $C_{1-6}$-alkyl lithium, such as hexyllithium, n-butyllithium and sec-butyllithium, followed by reaction with a compound of the formula (IV):

$$X—(CH_2)_m—Y \qquad (IV)$$

wherein Y is defined as in relation to formula (II), X is a chlorine, bromine or iodine atom or a mesylate, tosylate, brosylate, nosylate or triflate group, and m is 3 or 4 when $R^3$ is hydrogen, or m is 2 or 3 when $R^3$ is methyl.

It is a great advantage of the present invention that the above reactions may be performed as a "one pot" or single stage reaction.

In formulae (I), (II) and (III), R¹ is preferably a chlorine atom.

In formulae (I) and (II), n is most aptly 3.

In formulae (I), (II) and (III), suitable examples of the amino protecting group P include a group selected from: tert-butylmethoxyphenylsilyl, tert-butoxydiphenylsilyl, trimethylsilyl, triethylsilyl, acetyl, pivaloyl (2,2-dimethyl-1-oxopropyl), o-nitrobenzyloxycarbonyl, p-nitrobenzyloxycarbonyl, benzyloxycarbonyl, tert-butyloxycarbonyl (t-BOC), 2,2,2-trichloroethyloxycarbonyl, benzhydryl, o-nitrobenzyl, p-nitrobenzyl, 2-naphthylmethyl, benzyl, 2,2,2-trichloroethyl, tert-butyldimethylsilyl, tert-butyldiphenylsilyl, 2-(trimethylsilyl)ethyl, p-methoxybenzyl, p-methoxyphenyl, 4-pyridylmethyl, tert-butyl, allyloxycarbonyl, di-$C_{1-10}$ alkylphosphoryl, diarylphosphoryl and di-ar-$C_{1-10}$ alkylphosphoryl.

More particularly, P represents a protecting group which is selected from the group consisting of: an alkoxycarbonyl group (especially t-BOC), diisopropylphosphoryl and pivaloyl (2,2-dimethyl-1-oxopropyl).

Most suitably, P is a tert-butoxycarbonyl (t-BOC) group.

Hence, in a favoured embodiment, the present invention provides a process for the preparation of the compounds of the formulae (V) and (VI):

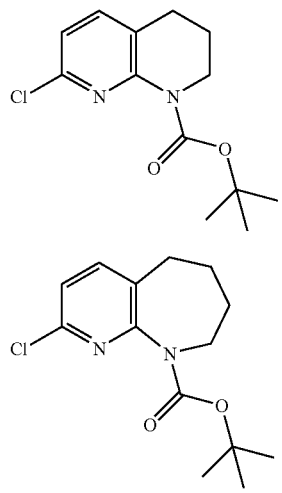

(V)

(VI)

which comprises the reaction of a compound of the formula (IV) as defined above with the compound of the formula (VII)

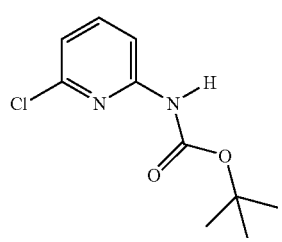

(VII)

to yield a compound of the formula (VIII)

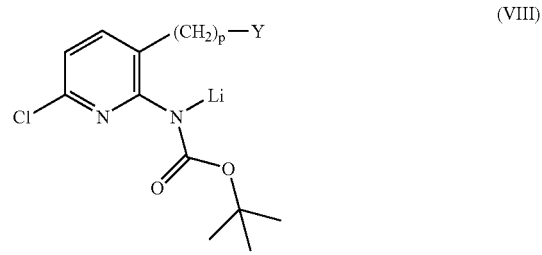

(VIII)

wherein Y is as defined in relation to formula (II) and p is 3 or 4, and which is cyclised, without isolation, to the compounds of formulae (V) and (VI), respectively.

In compounds of formula (IV), X and Y are suitably both halogen, for example X may be bromo or iodo and Y may be chloro. Apt compounds include $Cl(CH_2)_4I$, $Cl(CH_2)_3I$, $Cl(CH_2)_2I$, $Cl(CH_2)_4Br$, $Cl(CH_2)_3Br$ and $Cl(CH_2)_2Br$.

The compounds of the formulae (III) and (VII) may be prepared from the corresponding carbamates of formulae (IX) and (X), wherein BOC is $CO_2{}^tBu$:

(IX)

(X)

by reaction with a lithium alkyl such as a slight excess of n-BuLi or s-BuLi preferably in the presence of equimolar amount of tetramethylethylenediamine.

The compounds of formula (I) may be converted into compounds of International Patent Publication No. WO 00/72801 by the synthetic methods described therein and by other conventional chemical synthetic methods.

The compounds of formula (I) are also useful intermediates in the preparation of compounds of U.S. Pat. No. 3,960,876 and can be used as described therein.

The present invention further describes a practical method to prepare enantiopure compounds of the formula (XI):

(XIa)

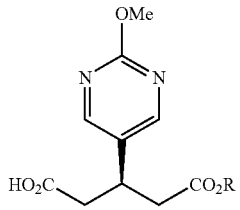

(XIb)

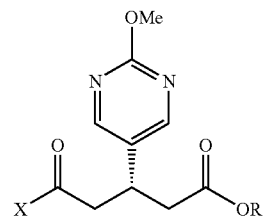

(XIII)

and salts thereof wherein R is an esterifying group. Most suitably, R is a $C_{1-6}$ alkyl group such as methyl, ethyl or propyl group and is preferably a methyl group.

Compounds of formula (XI) may be prepared by the asymmetric solvolysis of the anhydride of the formula (XII):

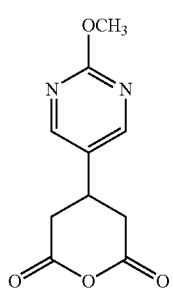

(XII)

This reaction may be performed using lower alkanols such as methanol, ethanol, 2,2,2-trifluoroethanol, 1-propanol, benzyl alcohol, 2-propanol and 1,1,1,3,3,3-hexafluoro-2-propanol at a temperature between −70° C. and ambient temperature. Preferably, the reaction is carried out with methanol at about −30° C. The reaction will use a solvent which can be an excess of the lower alkanol but which is preferably an inert solvent such as THF, DMF, dichloromethane or toluene. Generally about 10 equivalents of the alkanol will be used and the reaction adjusted to a concentration of about 0.2-0.4 M. The reaction is performed in the presence of a catalytic or stoichiometric amount of an optically active amine. The amine is typically a naturally occurring Cinchona alkaloid or one of its derivatives and is most suitably present in an equimolar amount. Preferred amines include quinidine and quinine. Hence the compound of formula (XIa) is favourably formed as the quinidine salt. On the other hand, the compound of formula (XIb) can be obtained with quinine. It is an important advantage of the current invention that the diastereomeric purity of the amine salts can in principle be conveniently increased via a recrystallization.

This invention also provides a practical procedure to prepare the compound of formula (m as well as methods to convert compounds of the formula (XIa) or (XIb) into compounds of the formula (XIII):

wherein R is as defined in relation to formula (XI) and X is (a) a —$CH_2P(O)(OR')_2$ group, wherein R' is defined as a $C_{1-6}$alkyl group such as methyl, ethyl, propyl, isopropyl, etc. or (b) a $Ph_3P=CH$— group.

The compounds of formula (XIIIa) wherein X is —$CH_2P(O)(OR')_2$ may be prepared from the compounds of formula (XIa) by an activation reaction with pivaloyl chloride and triethylamine in dry THF at −5° C., yielding a compound of formula (XIII) wherein X is —$O.CO.C(CH_3)_3$, followed by a reaction with an excess of lithiated dialkylmethylphosphonate at low temperature. Alternatively, compounds of formula (XIIIa) can be prepared by a reaction of compounds of the formula (XIb) with an excess of lithiated dialkylmethylphosphonate at low temperature followed by an esterification.

The compound of formula (XIIIb) wherein X is $Ph_3P=CH$— may be prepared from the compounds of formula (XIa) by an activation reaction with either pivaloyl chloride or isobutylchloroformate and a suitable base (triethylamine, diisopropylethylamine, etc.) in dry THF at about −5° C., yielding compounds of formula (XIII) wherein X is —$O.CO.C(CH_3)_3$ and —$OCO_2{}^iBu$, respectively, followed by a reaction with an excess of lithiated $Ph_3P^{\oplus}CH_3.Br^{\ominus}$ in THF at about −70° C. and then allowing the reaction to warm to ambient temperature. The excess lithiated $Ph_3P^{\oplus}CH_3.Br^{\ominus}$ can range from 2.2 to 3.5 equivalents depending on whether or not the triethylamine hydrochloride salt which is formed in the activation step is removed (via filtration or extraction).

The compounds of formulae (XI) and (XIII) are at least 60% enantiomerically pure, more suitably at least 80% enantiomerically pure, preferably at least 90% enantiomerically pure and most preferably at least 98% enantiomerically pure.

The compound of formula (XII) may be prepared by treating the corresponding diacid of formula (XIV)

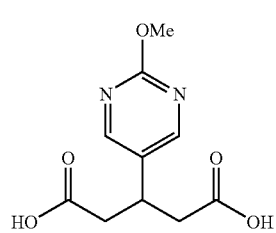

(XIV)

with trifluoroacetic anhydride in a suitable inert solvent, such as THF at an elevated temperature, such as between 50 and 55° C. Crystallisation by slow addition of an antisolvent, such as heptane followed by cooling, for instance to ambient temperature, results in good yield.

The diacid of formula (XIV) may be prepared by reacting 2-methoxypyrimidine-5-carbaldehyde with ethylacetoacetate in the presence of piperidine in a suitable solvent, such as an alcohol, for example, propan-2-ol, at a temperature in the range of 10-80° C., preferably at 50° C. The reaction is followed by a hydrolysis with, for instance, aqueous sodium hydroxide at 0° C., phase separation of the resulting mixture, acidification of the aqueous layer with, for instance, concentrated hydrochloric acid to pH 2-3 and crystallization of the product.

The compounds of the formulae (XIIIa) and (XIIIb) are useful intermediates to prepare the compound of formula (A) via a reaction with the compound of formula (XV)

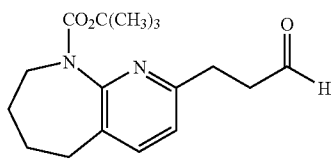

(XV)

and further elaboration of the resulting product to give the desired active pharmaceutical ingredient.

The present invention further describes a practical method to prepare enantiopure compounds of the formula (A) which comprises reacting a compound of formula (XVI) with a compound of formula (XIII):

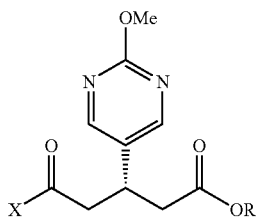

(XVI)

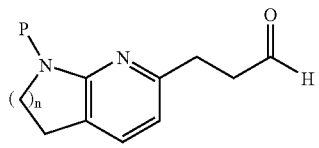

(XIII)

wherein n is 2 or 3, P is an amino protecting group, and R and X are as hereinbefore defined for the compound of formula (XIII); followed by enone reduction and deprotection of the carboxyl and amino groups.

Preferably n is 3.

Suitable examples of the amino protecting group P include a group selected from: tert-butylmethoxyphenylsilyl, tert-butoxydiphenylsilyl, trimethylsilyl, triethylsilyl, acetyl, pivaloyl (2,2-dimethyl-1-oxopropyl), o-nitrobenzyloxycarbonyl, p-nitrobenzyloxycarbonyl, benzyloxycarbonyl, tert-butyloxycarbonyl (t-BOC), 2,2,2-trichloroethyloxycarbonyl, benzhydryl, o-nitrobenzyl, p-nitrobenzyl, 2-naphthylmethyl, benzyl, 2,2,2-trichloroethyl, tert-butyldimethylsilyl, tert-butyldiphenylsilyl, 2-(trimethylsilyl)ethyl, p-methoxybenzyl, p-methoxyphenyl, 4-pyridylmethyl, tert-butyl, allyloxycarbonyl, di-$C_{1-10}$ alkylphosphoryl, diarylphosphoryl and di-ar-$C_{1-10}$ alkylphosphoryl.

More particularly, P represents a protecting group which is selected from the group consisting of: an alkoxycarbonyl group (especially t-BOC), diisopropylphosphoryl and pivaloyl (2,2-dimethyl-1-oxopropyl).

Most suitably, P is a tert-butoxycarbonyl (t-BOC) group.

Most suitably, R is a $C_{1-6}$ alkyl group such as methyl, ethyl or propyl group and is preferably a methyl group.

Preferably, X is —CH=PPh$_3$.

The reaction is conveniently effected as a single solvent through-process. Suitable solvents include toluene, isopropyl acetate, acetonitrile, ethanol and isopropyl alcohol (2-propanol), the latter being most preferred.

Conveniently, the intermediate enone of formula (XVII)

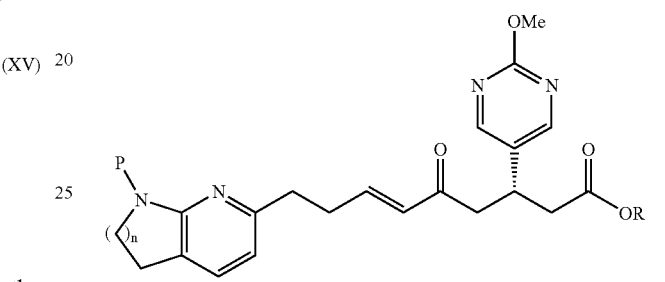

(XVII)

is not isolated. Enone reduction is conveniently effected by hydrogenation in the presence of a palladium metal catalyst, aptly palladium on carbon. After filtration of the catalyst, a saponification step using aqueous hydroxide, for example, sodium hydroxide, removes the carboxyl protecting group to give the compound of formula (XVIII)

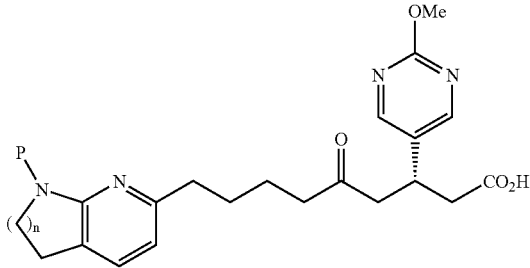

(XVIII)

Deprotection of compound (XIII) can be effected in a conventional manner. Preferably, when P is a tert-butoxycarbonyl (BOC) group, acids are used. Most preferably, a treatment with an excess of trifluoroacetic acid (preferably about 15 equivalents) is used. The reaction is effected in a suitable solvent. Preferably, a halogenated hydrocarbon, for example, dichloromethane, at a temperature between 20° C. and 40° C. is used.

After neutralizing the reaction mixture with aqueous hydroxide, for example, sodium hydroxide, and, if necessary, adjusting the pH of the separated aqueous layer to about 6.0 using a mineral acid, such as hydrochloric acid, the compound of formula (A) is extracted as the zwitterion using a suitable solvent, preferably dichloromethane.

Before or after deprotection of the amino moiety, the reaction mixture may undergo a carbon treatment to reduce the level of residual palladium.

The compound of formula (A) may be crystallized from a lower alkanol solvent. Ethanol and 2-propanol are the preferred solvents; 2-propanol is the most preferred solvent.

Figure 3:
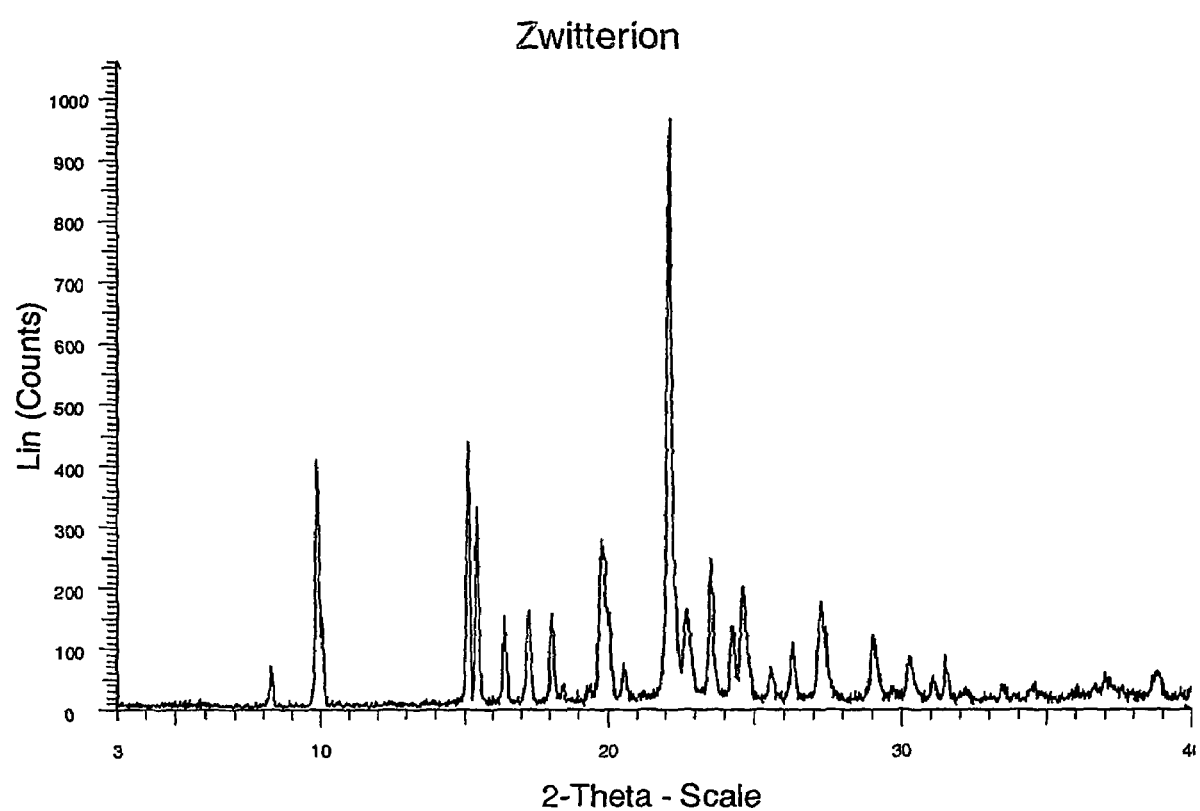
FIG. 3 is an x-ray powder diffraction (XRPD) pattern for the crystalline zwitterion of the compound of formula (A) where n=3 containing all observed XRPD reflections between 3° and 40° 2-theta. The ordinate or Y-axis is x-ray intensity (counts) and the abscissa or X-axis is the angle two-theta (2θ) in degrees.

The novel, crystalline zwitterion of the compound of formula (A) is unexpectedly stable and non-hygroscopic, and has a desirable water solubility making it particularly advantageous for pharmaceutical formulation. The crystalline zwitterion of the compound of formula (A) where n=3 is characterised by the X-ray powder diffraction (XRPD) data shown in FIG. 3, which has the significant peaks listed in Table 1:

TABLE 1

| Angle 2-Theta ° | d value Angstrom | Intensity Count |
|---|---|---|
| 9.8 | 8.98 | 408 |
| 15.1 | 5.86 | 439 |
| 15.5 | 5.73 | 331 |
| 16.4 | 5.40 | 151 |
| 17.3 | 5.13 | 160 |
| 18.1 | 4.89 | 138 |
| 19.8 | 4.48 | 278 |
| 22.1 | 4.01 | 965 |
| 23.5 | 3.78 | 247 |
| 24.6 | 3.61 | 202 |
| 27.3 | 3.27 | 176 |

Although crystalline zwitterion of the compound of formula (A) where n=3 is characterized by the complete group of angle 2 theta values listed in Table 1, all the values are not required for such identification. The crystalline zwitterion of the compound of formula (A) where n=3 can be identified by the most significant angle 2 theta values: 9.8°, 15.1°, 15.5°, 19.8°, 22.1°, 23.5° and 24.6°.

The compound of formula (A) may also be crystallized as the tris(hydroxymethyl)aminomethane (TRIS) salt by treating a solution of the zwitterion (for instance, in 2-propanol) with tris(hydroxymethyl)aminomethane and then crystallizing the TRIS salt from either ethanol or, more preferably, 2-propanol. The crystallization solvent may be "wet" or "dry", i.e. containing a water content of between about 6% and less than 0.1%, preferably about 4%.

Figure 4:
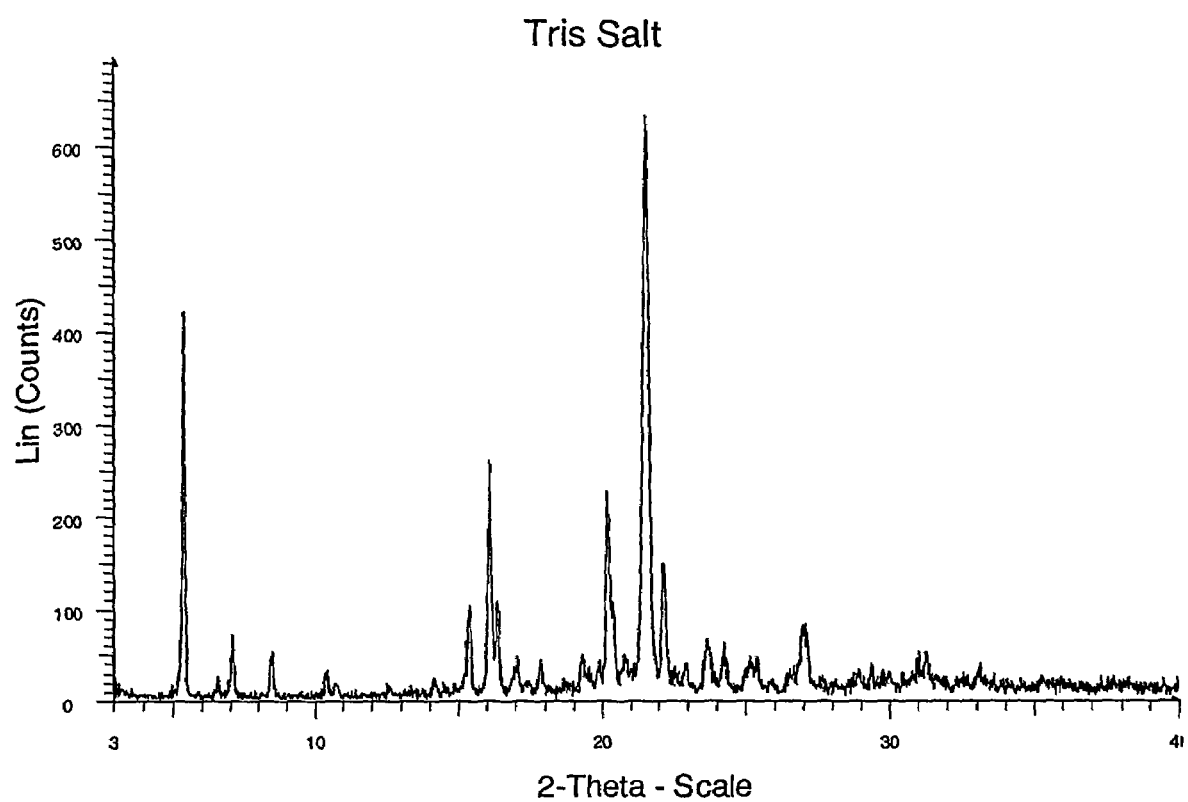
FIG. 4 is an x-ray powder diffraction (XRPD) pattern for the crystalline TRIS salt of the compound of formula (A) where n=3 containing all observed XRPD reflections between 3° and 40° 2-theta. The ordinate or Y-axis is x-ray intensity (counts) and the abscissa or X-axis is the angle two-theta (2θ) in degrees.

The novel, crystalline TRIS salt of the compound of formula (A) where n=3 is characterised by the XRPD data shown in FIG. 4, which has the significant peaks listed in Table 2:

TABLE 2

| Angle 2-Theta ° | d value Angstrom | Intensity Count |
|---|---|---|
| 5.3 | 16.56 | 422 |
| 15.4 | 5.76 | 102 |
| 16.1 | 5.51 | 259 |
| 20.2 | 4.39 | 227 |
| 21.5 | 4.13 | 633 |
| 22.1 | 4.01 | 147 |

Although crystalline TRIS salt of the compound of formula (A) where n=3 is characterized by the complete group of angle 2 theta values listed in Table 2, all the values are not required for such identification. The crystalline TRIS salt of the compound of formula (A) where n=3 can be identified by the most significant angle 2 theta values: 5.3°, 16.1°, 20.2° and 21.5°.

If desired, the crystallization of the TRIS salt of the compound of formula (A) may be utilised in a method of purifying the zwitterion of the compound of formula (A). Thus, the zwitterion is prepared as previously described, and is converted to the TRIS salt as described above. After recovery of the crystalline TRIS salt, the salt is broken by dissolving the TRIS salt in de-ionized water. The pH is adjusted to about 6.0 using, for example, hydrochloric acid, and the solution extracted with dichloromethane. After washing with further de-ionized water, the solvent is switched and the product crystallized as described above.

If desired, a carbon treatment stage may be incorporated into the zwitterion recrystallization using a suitable carbon.

The crystalline zwitterion compound of formula (A) prepared in the above method has a very high enantiopurity, with an enantiomeric excess of ≧98%, preferably ≧99%, and more preferably ≧99.5%.

According to a further aspect of the present invention, compounds of formula (XVI) may be prepared by a Suzuki coupling of the compounds of formulae (I) and (XIX), wherein $R^1$ is a chlorine atom and each $R^a$ is independently $C_1$ to $C_6$ straight or branched alkyl, preferably methyl or ethyl and P is defined as above,

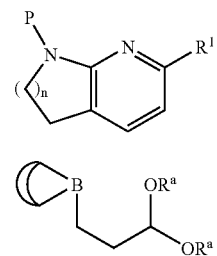

followed by acetal hydrolysis to yield the compound of formula (XVI).

Conditions suitable for a Suzuki coupling reaction are well known in the art (for review, see for instance A. Suzuki, in "Metal-catalyzed Cross-coupling Reactions", F. Diederich and P. J. Stang (Eds.), Wiley-VCH; Weinheim (1998), pp 49-89), using a catalyst formed in situ from a suitable palladium salt and a ligand. Suitable catalysts include tetrakis(triphenylphosphine)palladium (0), the combination of palladium(II) acetate and 1,1'-bis(diphenylphosphanyl)ferrocene (DPPF) or the related dichloro[1,1'-bis(diphenylphosphino)ferrocene]palladium (II) dichloromethane adduct, or the combination of palladium(II) acetate and tricyclohexylphosphine ($Cy_3P$), or the related bis(tricyclohexylphosphine)-palladium (0) or trans-dichlorobis(tricyclohexylphosphine)palladium (II).

A particularly preferred catalyst is that formed in situ from a combination of palladium(II) acetate and 1,1'-bis (diphenylphosphanyl)ferrocene (DPPF).

The reaction is effected in the presence of a base, for example, potassium carbonate, sodium tert-butoxide or aqueous sodium hydroxide, in a suitable solvent such as an ether, for example, tetrahydrofuran, dimethoxyethane or dioxane or an aromatic hydrocarbon, for example toluene, and at an elevated temperature, for example, between 65° C. and the reflux temperature of the solvent.

A particularly preferred base is potassium carbonate.

Immediately following the coupling reaction acetal hydrolysis can be effected in high yield using conventional procedures, for example, by extracting the diethyl acetal intermediate into isopropyl acetate and treating with a strong acid such as hydrochloric acid, at a reduced temperature, for example, between 0° C. and 10° C.

The compound of formula (XIX) can be prepared from the commercially available acrolein dialkyl acetal, preferably the diethyl or dimethyl acetal, and 9-borabicyclo[3.3.1]

nonane (9-BBN) following a standard hydroboration protocol at 0 to 30° C. in an ether solvent, preferably tetrahydrofuran.

The compound of the formula (III) where $R^1$ is a chlorine atom may also be prepared from the corresponding protected amine of formula (XX)

by reaction with a lithium alkyl such as a slight excess of n-BuLi or s-BuLi, preferably in the presence of an equimolar amount of tetramethylethylenediamine.

The following non-limiting examples are provided to illustrate the present invention.

EXAMPLE 1

1,1-Dimethylethyl 2-chloro-5,6,7,8-tetrahydro-9H-pyrido[2,3-b]azepine-9-carboxylate

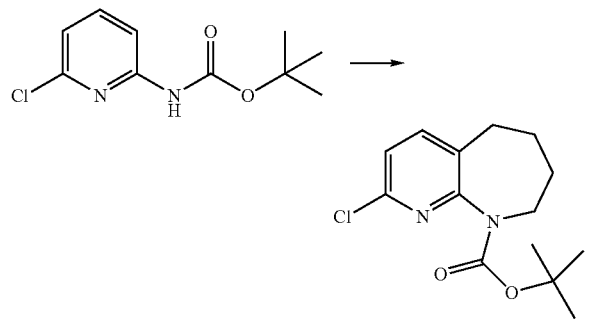

Tetramethylethylenediamine (5.85 kg) was dissolved in THF (54.5 L) and degassed. The bath was cooled to −20° C. and then hexyllithium (~2.5 M, 22 L) was charged over 35 minutes maintaining the internal temperature between −10° C. and −20° C. The batch was aged for 30 minutes between −18° C. to −16° C. and then cooled further to −75° C. A solution of 1,1-dimethylethyl[6-chloro-2-pyridinyl]carbamate (5.23 kg) in THF (16 L) was added to the above solution, maintaining the temperature below −65° C. The red/brown dianion solution was aged for 1 hour at −70° C. and then a solution of 1-chloro-4-iodobutane (7.57 kg) in THF (5 L) was added, maintaining the internal temperature below −65° C. After the addition, the reaction was allowed to warm slowly to ambient temperature and then heated to reflux for 9 hours. The solution was then cooled to 60° C. and water (54.5 kg) added, maintaining the internal temperature above 40° C. The aqueous layer was cut and extracted with isopropyl acetate (IPAc) (54.4 L). The combined organic layers were washed with water (27 L), azeotropically distilled iin vacuo to a volume of 26 L, and then solvent switched to heptane to a final volume of 26 L. The resulting slurry of crystals was cooled to 5° C., aged for 1 hour and then isolated by filtration. A wash with cold heptane (10 L) and overnight drying iin vacuo at 40° C. furnished the title compound (5.05 kg) in 78% yield. Recrystallisation from ethyl acetate furnished an analytically pure sample; m.p. 166-168° C.

$^1$H NMR (400 MHz, d$_6$-DMSO, 343 K): δ 7.62 (d, J=7.9 Hz, 1H), 7.17 (d, J=7.9 Hz, 1H), 3.35 (m, 2H), 2.58 (m, 2H), 1.62 (m, 2H), 1.51 (m, 2H), 1.22 (s, 9H); $^{13}$C NMR (100 MHz, d$_6$-DMSO, 343 K): δ 155.7, 153.8, 146.7, 142.8, 134.0, 123.3, 80.6, 47.1, 32.6, 29.5, 28.8, 25.7.

EXAMPLE 2

In all of the following reactions high yielding lithiation could be achieved by the addition of 1b to a slight excess (2.2 eq) of an equimolar TMEDA/n-BuLi solution, whereas the lithiation of 1a required more forcing conditions (TMEDA/n-BuLi at −10° C. or TMEDA/s-BuLi at −78° C.). The TMEDA/BuLi mixtures were aged for about 30 minutes at −20° C. prior to addition of substrate 1. The dianion is then quenched with the α,ω-dihalide to form the intermediate. Warming the reaction mixture to reflux effected ring closure to give the product 2. The results of a series of experiments were as follows:

TABLE 3

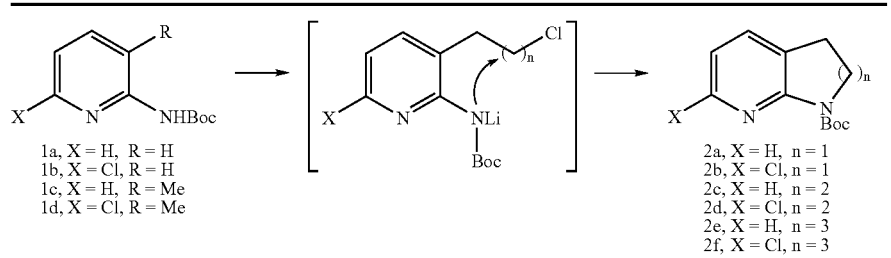

1a, X = H, R = H
1b, X = Cl, R = H
1c, X = H, R = Me
1d, X = Cl, R = Me

2a, X = H, n = 1
2b, X = Cl, n = 1
2c, X = H, n = 2
2d, X = Cl, n = 2
2e, X = H, n = 3
2f, X = Cl, n = 3

| Entry | Substrate 1 | R—Li | Additive | Copper (I) Halide | Electrophile | Product 2 | Yield %$^a$ |
|---|---|---|---|---|---|---|---|
| 1 | 1a | s-BuLi | TMEDA | — | Cl(CH$_2$)$_2$I | 2a | 0 |
| 2 | 1a | s-BuLi | TMEDA | — | Cl(CH$_2$)$_3$I | 2c | 54 |
| 3 | 1a | s-BuLi | TMEDA | — | Cl(CH$_2$)$_4$I | 2e | 55 |
| 4 | 1d | n-BuLi | — | — | Cl(CH$_2$)$_2$I | 2d | 0 |
| 5 | 1c | n-BuLi | — | — | Cl(CH$_2$)$_3$I | 2e | 86 |
| 6 | 1c | n-BuLi | — | — | Cl(CH$_2$)$_2$Br | 2c | 0 |
| 7 | 1b | n-BuLi | TMEDA | — | Cl(CH$_2$)$_4$Br | 2f | 51 |

TABLE 3-continued

| Entry | Substrate 1 | R—Li | Additive | Copper (I) Halide | Electrophile | Product 2 | Yield %[a] |
|---|---|---|---|---|---|---|---|
| 8 | 1b | n-BuLi | TMEDA | — | Cl(CH$_2$)$_3$I | 2d | 51 |
| 9 | 1b | n-BuLi | TMEDA | — | Cl(CH$_2$)$_4$I | 2f | 85 |
| 10 | 1b | n-BuLi | TMEDA | — | MeI | 1d | 91 |
| 11 | 1b | n-BuLi | TMEDA | CuCl | Cl(CH$_2$)$_3$I | 2d | 95 (91) |
| 12 | 1b | n-BuLi | TMEDA | CuBr | Cl(CH$_2$)$_3$I | 2d | 94 |
| 13 | 1b | n-BuLi | TMEDA | CuBr•Me$_2$S | Cl(CH$_2$)$_3$I | 2d | 94 |
| 14 | 1b | n-BuLi | TMEDA | CuI | Cl(CH$_2$)$_3$I | 2d | 98 |
| 15 | 1b | n-BuLi | TMEDA | CuBr•Me$_2$S | Cl(CH$_2$)$_4$I | 2f | 90 (86) |
| 16 | 1b | n-BuLi | TMEDA | CuBr | Cl(CH$_2$)$_2$I | 2b | 57 |
| 17 | 1b | n-BuLi | TMEDA | CuBr•Me$_2$S | Cl(CH$_2$)$_2$I | 2b | 57 |

[a]Yield refers to HPLC assay yield, obtained by comparison with an isolated pure standard. Yield in parentheses refers to isolated yield, either by silica gel chromatograph or crystallisation.

EXAMPLE 3

4-Carboxy-3-(2-methoxypyrimidin-5-yl)butanoic acid

2-Methoxypyrimidine-5-carbaldehyde (see *J. Heterocycl. Chem.* (1991) 28, 1281) (9.00 kg) was reacted with ethylacetoacetate (17.8 kg) in the presence of piperidine (555 g) in propan-2-ol (90 L) at 50° C. for several hours, followed by a hydrolysis with aqueous sodium hydroxide (24.2 kg of 46% NaOH in 30 L of water) at 0° C. Phase separation of the resulting mixture, acidification of the aqueous layer with concentrated hydrochloric acid (23.2 kg) to pH 2-3 and crystallization afforded the title compound (12.7 kg; 85% yield).

$^1$H NMR (250 MHz, methanol-d$_4$) δ 8.52 (s, 2 H), 3.98 (s, 3 H), 3.54 (tt, J=9.2, 6.1 Hz, 1H), 2.82 (dd, J=16.2, 6.1 Hz, 2 H), 2.67 (dd, J=16.2, 9.2 Hz, 2 H); $^{13}$C NMR 63 MHz, methanol-d$_4$) δ 174.9, 165.9, 160.2, 131.4, 55.6, 40.5, 34.6.

EXAMPLE 4

4-(2-Methoxypyrimidin-5-yl)glutaric anhydride

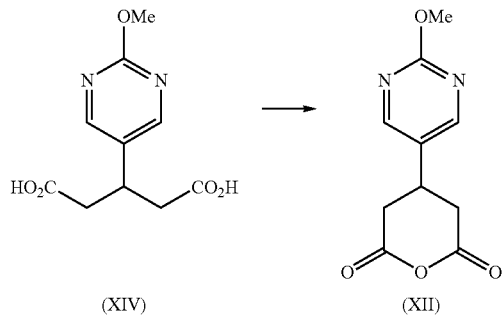

4-Carboxy-3-(2-methoxypyrimidin-5-yl)butanoic acid (11.5 kg) was treated with trifluoroacetic anhydride (12.1 kg) in THF (58 L) at 50-55° C. for several hours. Slow addition of heptane (195 L) followed by cooling to ambient temperature resulted in the crystallization of the title compound; 94% yield.

$^1$H NMR (250 MHz, CD$_2$Cl$_2$) δ 8.41 (s, 2 H), 3.99 (s, 3 H), 3.49-3.35 (m, 1 H), 3.18-3.07 (m, 2 H), 2.92-2.79 (m, 2 H); $^{13}$C NMR (63 MHz, CD$_2$Cl$_2$) δ 165.3, 164.9, 157.4, 125.6, 54.8, 36.2, 29.2.

EXAMPLE 5

(3S)-4-(Methoxycarbonyl)-3-(2-methoxypyrimidin-5-yl)butanoic acid

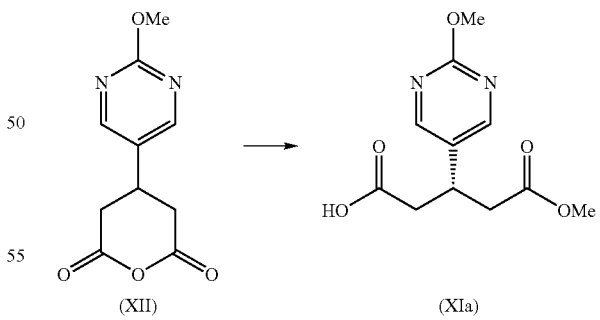

Toluene (180 L) was charged to a vessel containing anhydride (XII) (9.0 kg) and quinidine (13.15 kg) under a nitrogen atmosphere. The resulting slurry was cooled, with stirring, to −40° C. Methanol (13.0 kg), which had been pre-cooled to approx. 5° C., was then added over 15 minutes. The resulting reaction mixture was held at about −35° C. for 8 hours and then allowed to warm to ambient temperature overnight.

The reaction mixture was then extracted twice with water (2×60 L). The combined aqueous extracts were acidified with concentrated hydrochloric acid (4.0 kg), then seeded with the authentic product (45 g) before another portion of concentrated hydrochloric acid (4.0 kg) was added. The temperature of the resulting slurry was adjusted to 20° C., aged for 2 hours and then filtered to afford 6.54 kg of 98% e.e. pure crystalline product (63% yield).

$^1$H NMR (250 MHz, methanol-$d_4$) δ 8.52 (s, 2 H), 3.98 (s, 3 H), 3.62-3.48 (m, 1 H), 3.59 (s, 3 H), 2.85 (dd, J=16.2, 11.6 Hz, 1 H), 2.82 (dd, J=16.3, 11.7 Hz, 1 H), 2.73 (dd, J=16.2, 9.0 Hz, 1 H), 2.67 (dd, J=16.2, 9.0 Hz, 1 H); $^{13}$C NMR (63 MHz, methanol-$d_4$) δ 174.8, 173.5, 165.9, 160.2, 131.3, 55.6, 52.3, 40.4, 40.4, 34.6.

Two polymorphic crystal forms of (XIa) have been identified. Form A is characterized by a melting point of 148° C. and having an XRPD pattern at (FIG. 1), which has the significant peaks listed in Table 4:

TABLE 4

| Angle 2-Theta ° | d value Angstrom | Intensity Count |
|---|---|---|
| 9.4 | 9.40 | 686 |
| 14.2 | 6.23 | 727 |
| 14.6 | 6.04 | 633 |
| 15.1 | 5.88 | 280 |
| 18.2 | 4.88 | 193 |
| 19.5 | 4.55 | 850 |
| 19.9 | 4.46 | 249 |
| 22.2 | 4.00 | 246 |
| 23.1 | 3.85 | 2009 |
| 26.7 | 3.33 | 2221 |
| 28.4 | 3.14 | 1674 |
| 30.4 | 2.94 | 244 |

Figure 2:
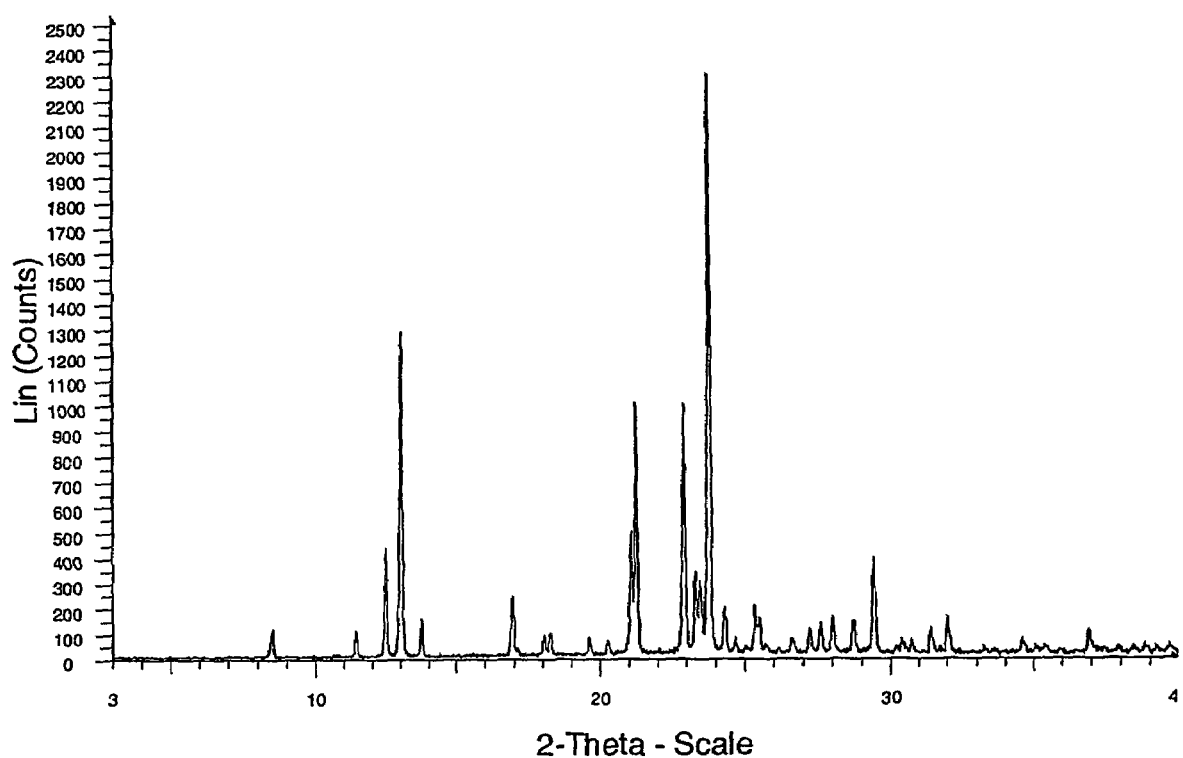
FIG. 2 is an x-ray powder diffraction (XRPD) pattern for the Form B polymorph of the product of Example 5 containing all observed XRPD reflections between 3° and 40° 2-theta. The ordinate or Y-axis is x-ray intensity (counts) and the abscissa or X-axis is the angle two-theta (2θ) in degrees.

Form B is characterized by a melting point of 145° C. and having an XRPD pattern at (FIG. 2), which has the significant peaks listed in Table 5:

TABLE 5

| Angle 2-Theta ° | d value Angstrom | Intensity Count |
|---|---|---|
| 12.5 | 7.10 | 435 |
| 13.0 | 6.81 | 1289 |
| 13.7 | 6.45 | 158 |
| 16.9 | 5.24 | 241 |
| 21.2 | 4.18 | 1008 |
| 22.9 | 3.88 | 1002 |
| 23.7 | 3.74 | 2306 |
| 29.4 | 3.03 | 394 |

EXAMPLE 6

Methyl (3S)-3-(2-methoxypyrimidin-5-yl)-5-oxo-6-(triphenylphosphoranylidene)hexanoate

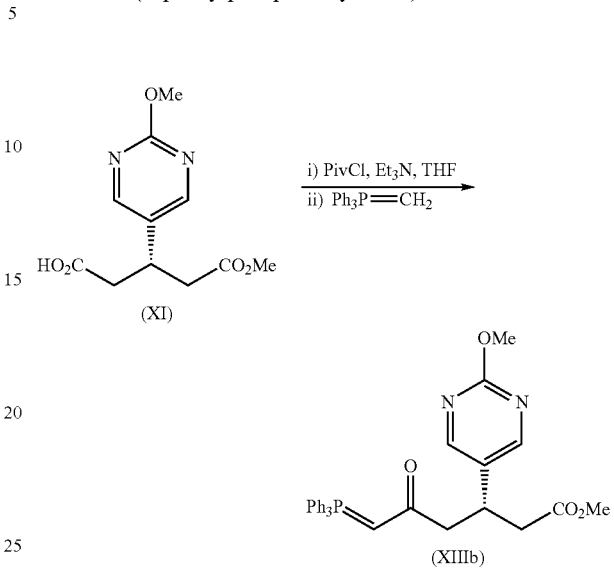

A suspension of methyltriphenylphosphonium bromide (18.2 kg) in THF (82 L) was cooled to −60° C. Hexyllithium (13.8 kg) was then added over 30 minutes, while keeping the internal temperature below −10° C. Once the addition was complete, the batch was aged at 0° C. for 90 minutes and then cooled to −80° C. and held awaiting the mixed anhydride formation.

A solution of acid-ester (XI) (4.38 kg) and trimethylacetyl chloride (2.06 kg) in THF (34 L) was cooled to −5° C. and triethylamine (1.72 kg) was added over a period of 30 minutes. After a rinse with THF (0.5 L), the resulting slurry was aged between −5 and 0° C. for 30 minutes and then added to the above ylide mixture whilst maintaining the internal temperature at approximately −70° C. The mixed anhydride vessel was rinsed with THF (8 L) and this rinse was also added to the batch.

After an age of 40 minutes the reaction mixture was transferred into an aqueous solution of potassium dihydrogenphosphate (1.20 kg $KH_2PO_4$ in 64 L of water), keeping the temperature of the quenched mixture between 0 and 10° C. Isopropyl acetate (IPAc) (85 L) was added to the quenched reaction mixture and the two phases were separated. The aqueous layer was further extracted with IPAc (85 L) and the combined organic extracts were then washed twice with half-saturated brine (6.95 kg NaCl in 38 L of water, each). The resulting organic layer was concentrated under reduced pressure to a volume of 25 L. IPAc (34 L) was added and the batch was again concentrated until a final volume of 25 L was reached. Crystallization of the product had occurred during this distillation and, after cooling to 0° C., the solid was collected by filtration, washing the wet-cake with MTBE (10.5 L). Drying overnight, under vacuum, at 30° C. afforded 6.28 kg of phosphorane (XIIIb) (70% corrected yield) as cream-coloured crystals.

$^1$H NMR (250 MHz, $CD_2Cl_2$) δ 8.33 (s, 2 H), 7.52-7.28 (m, 15 H), 3.88 (s, 3 H), 3.60-3.48 (m, 2 H), 3.47 (s, 3 H), 2.70 (dd, J=15.7, 5.9 Hz, 1 H), 2.58-2.45 (m, 3 H); $^{13}$C NMR (63 MHz, $CD_2Cl_2$) δ 189.3 (d, J=2 Hz), 172.4, 165.0, 159.1, 133.3 (d, J=10 Hz), 132.5 (d, J=3 Hz), 130.6, 129.1 (d, J=12 Hz), 127.3 (d, J=91 Hz), 55.0, 53.2 (d, J=107 Hz), 51.8, 46.8 (d, J=16 Hz), 40.7, 34.8.

EXAMPLE 7

1,1-Dimethylethyl 2-chloro-5,6,7,8-tetrahydro-9H-pyrido[2,3-b]azepine-9-carboxylate

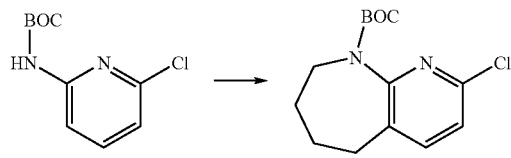

Tetramethylethylenediamine (5.85 kg) was dissolved in THF (54.5 L) and degassed. The bath was cooled to −20° C. and then hexyllithium (~2.5 M, 22 L) was charged over 35 minutes maintaining the internal temperature between −10° C. and −20° C. The batch was aged for 30 minutes between −18° C. to −16° C. and then cooled further to −75° C. A solution of 1,1-dimethylethyl[6-chloro-2-pyridinyl]carbamate (5.23 kg) in THF (16 L) was added to the above solution, maintaining the temperature below −65° C. The red/brown dianion solution was aged for 1 hour at −70° C. and then a solution of 1-chloro-4-iodobutane (7.57 kg) in THF (5 L) was added, maintaining the internal temperature below −65° C. After the addition, the reaction was allowed to warm slowly to ambient temperature and then heated to reflux for 9 hours. The solution was then cooled to 60° C. and water (54.5 kg) added, maintaining the internal temperature above 40° C. The aqueous layer was cut and extracted with IPAc (54.4 L). The combined organic layers were washed with water (27 L), azeotropically distilled in vacuo to a volume of 26 L, and then solvent switched to heptane to a final volume of 26 L. The resulting slurry of crystals was cooled to 5° C., aged for 1 hour and then isolated by filtration. A wash with cold heptane (10 L) and overnight drying in vacuo at 40° C. furnished the title compound (5.05 kg) in 78% yield. Recrystallisation from ethyl acetate furnished an analytically pure sample; m.p. 166-168° C.

$^1$H NMR (400 MHz, $d_6$-DMSO, 343 K): δ 7.62 (d, J=7.9 Hz, 1H), 7.17 (d, J=7.9 Hz, 1H), 3.35 (m, 2H), 2.58 (m, 2H), 1.62 (m, 2H), 1.51 (m, 2H), 1.22 (s, 9H); $^{13}$C NMR (100 MHz, $d_6$-DMSO, 343 K): δ 155.7, 153.8, 146.7, 142.8, 134.0, 123.3, 80.6, 47.1, 32.6, 29.5, 28.8, 25.7.

EXAMPLE 8 tert-Butyl 2-(3-oxopropyl)-5,6,7,8-tetrahydropyrido[2,3-b]azepine-9-carboxylate

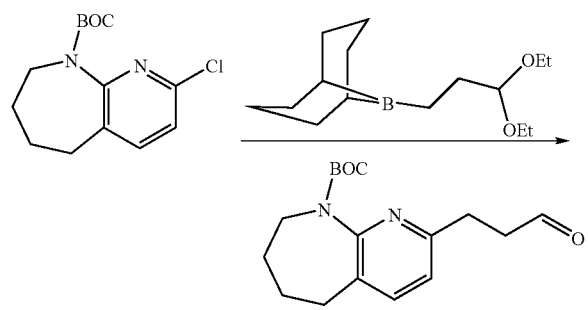

Acrolein diethyl acetal (3.51 kg) was added over 30 minutes to 0.41 M 9-BBN in THF (57.4 L) which had been pre-cooled to 0° C. The resulting reaction mixture was warmed to room temperature and then aged for 5 hours to give the hydroborated acrolein acetal.

A suspension of 1,1-dimethylethyl 2-chloro-5,6,7,8-tetrahydro-9H-pyrido[2,3-b]azepine-9-carboxylate (3.32 kg), potassium carbonate (3.25 kg), palladium acetate (132 g) and 1,1'-bis(diphenylphosphanyl)ferrocene (dppf) ((326 g) in THF (16.5 L) was degassed and put under an atmosphere of nitrogen. The THF solution of the hydroborated acrolein acetal was then added. The reaction mixture was degassed, purged with nitrogen and then heated at reflux for 26 hours. The reaction mixture was then cooled to 20° C., water (66 L) was added and the mixture was stirred for 30 minutes. The two layers were allowed to settle and the lower aqueous phase was discarded. IPAc (10 L) was then added and, after stirring for 5 minutes and allowing the mixture to settle, the lower aqueous phase was again discarded. The resulting organic layer was concentrated by distillation under reduced pressure to minimum volume (55 L of distillate removed) and a second portion of IPAc (33 L) was then charged. The two layers were again separated, the aqueous phase was discarded and the remaining organic layer was concentrated to minimum volume (10 L) under reduced pressure. IPAc (23 L) was added and the mixture held overnight at ambient temperature. The solution was cooled to 0° C. and treated with pre-cooled (0° C.) 2M hydrochloric acid (23.0 L), while keeping the temperature below 10° C. The resulting two phase mixture was stirred at 0° C. for 4 hours.

The mixture was allowed to settle and the phases separated. The aqueous phase was filtered, cooled to 0-5° C. and IPAc (16.5 L) added. The mixture was then basified (to pH 8) by addition of 10% aqueous potassium carbonate (5.5 kg dissolved in 49.5 L of water). The mixture was agitated for 5 minutes, allowed to settle and the phases separated. The aqueous phase was extracted with IPAc (2×16.5 L) and the combined IPAc extracts were washed with water (8.25 L). The IPAc solution was concentrated by distillation under reduced pressure to low volume (ca. 10 L). Isopropanol (33 L) was added and the solution again distilled to low volume under reduced pressure. Additional isopropanol (33 L) was added and the solution concentrated to about 15 L by distillation under reduced pressure. The isopropanol solution was then assayed for the desired aldehyde (yield: 3.075 kg; 86%).

EXAMPLE 9 tert-Butyl 2-[(7S)-8-methoxycarbonyl-7-(2-methoxypyrimidin-5-yl)-5-oxo-3-octenyl]-5,6,7,8-tetrahydropyrido[2,3-b]azepine-9-carboxylate

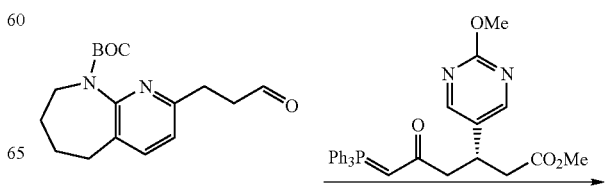

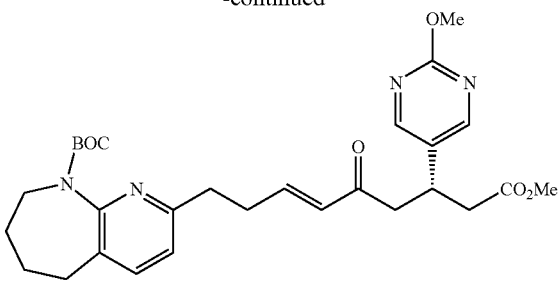

A solution of the priopionaldehyde of Example 8 (3.02 kg) in isopropanol (11.98 kg total mass) was charged to a vessel containing methyl (3S)-3-(2-methoxypyrimidin-5-yl)-5-oxo-6-(triphenylphosphoranylidene)hexanoate (Example 6; 4.84 kg). The resulting slurry was degassed, put under an atmosphere of nitrogen and then heated to reflux. The resulting clear solution was aged for 12 hours. The reaction mixture was allowed to cool to room temperature overnight and directly used in Example 10 without isolation of the intermediate enone.

$^1$H NMR (250 MHz, CD$_2$Cl$_2$) δ 8.37 (s, 2 H), 7.46 (d, J=7.6 Hz, 1 H), 6.94 (d, J=7.6 Hz, 1 H), 6.86 (dt, J=15.9, 6.7 Hz, 1 H), 6.06 (dt, J=15.9, 1.5 Hz, 1 H), 3.94 (s, 3 H), 3.7-3.2 (br, 2H), 3.69-3.55 (m, 1 H), 3.57 (s, 3 H), 3.02-2.81 (m, 4 H), 2.78-2.53 (m, 6 H), 1.88-1.75 (m, 2 H), 1.72-1.55 (m, 2 H), 1.38 (s, 9H); $^{13}$C NMR (63 MHz, CD$_2$Cl$_2$) δ 197.5, 171.9, 165.1, 158.9, 157.7, 155.5, 154.1, 147.5, 139.3, 132.5, 130.8, 130.0, 121.6, 80.0, 55.1, 52.0, 47.2, 45.3, 40.1, 36.2, 33.5, 32.6, 32.3, 29.9, 28.4, 26.4.

EXAMPLE 10 tert-Butyl 2-[(7S)-8-methoxycarbonyl-7-(2-methoxypyrimidin-5-yl)-5-oxooctyl]-5,6,7,8-tetrahydropyrido[2,3-b]azepine-9-carboxylate

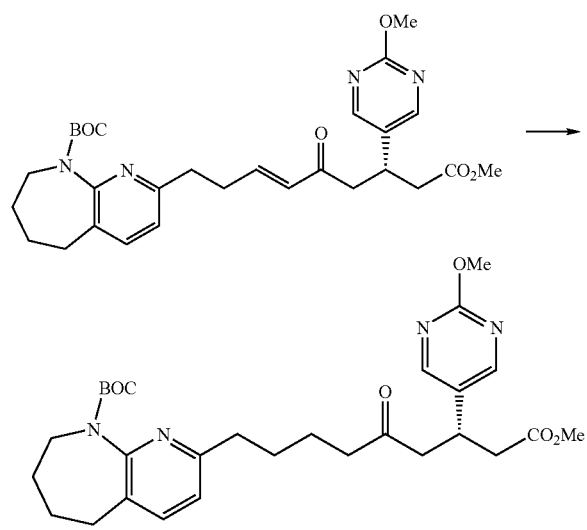

The solution of the enone intermediate of Example 9 in isopropanol was charged to a hydrogenation vessel under an atmosphere of nitrogen. A slurry of wet (58 wt % water) palladium on carbon catalyst (1.27 kg) in isopropanol (10 L) was added, washing with further isopropanol (15 L). After degassing the resulting reaction mixture was hydrogenated at 2.8 bar for 2 hours. The catalyst was filtered and washed with isopropanol (4×15 L). The combined filtrates (88.0 kg) were concentrated under reduced pressure to a total volume of ca. 20 L and the solution was directly used in Example 11 without isolation of the product.

$^1$H NMR (250 MHz, CD$_2$Cl$_2$) δ 8.37 (s, 2 H), 7.43 (d, J'7.6 Hz, 1 H), 6.92 (d, J=7.6 Hz, 1 H), 3.93 (s, 3 H), 3.9-3.0 (br, 2 H), 3.66-3.52 (m, 1H), 3.57 (s, 3 H), 2.90-2.62 (m, 7 H), 2.55 (dd, J=15.9, 8.7 Hz, 1 H), 2.45-2.28 (m, 2 H), 1.86-1.75 (m, 2 H), 1.70-1.49 (m, 6 H), 1.37 (s, 9H); $^{13}$C NMR (63 MHz, CD$_2$Cl$_2$) δ 208.2, 171.9, 165.1, 159.3, 158.9, 155.3, 154.1, 139.1, 132.0, 130.0, 121.5, 79.9, 55.1, 52.0, 47.9, 47.1, 43.3, 40.0, 37.6, 33.5, 32.0, 29.9, 29.5, 28.5, 26.5, 23.5.

EXAMPLE 11 tert-Butyl 2-[(7S)-8-carboxy-7-(2-methoxypyrimidin-5-yl)-5-oxooctyl]-5,6,7,8-tetrahydropyrido[2,3-b]azepine-9-carboxylate

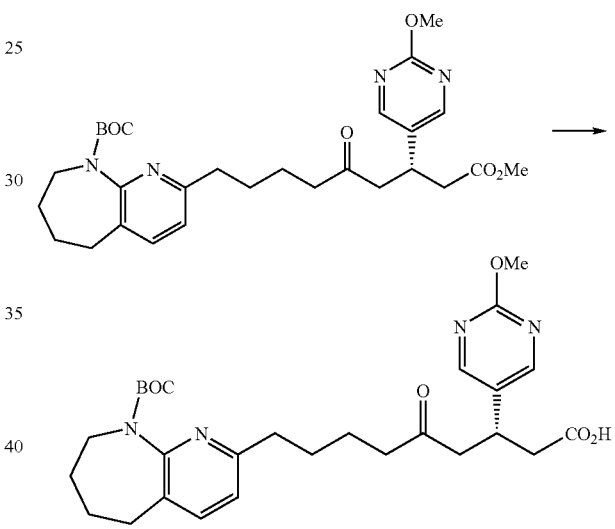

The solution of the BOC-protected methyl ester in isopropanol (ca. 20 L) from Example 10 (4.50 kg) was cooled to 0° C. 2M Sodium hydroxide (5.6 L) was added and the resulting reaction mixture aged at 0° C. for 2 hours. The resulting thin slurry was diluted with water (43 L) and warmed to 20° C. The resulting aqueous solution was washed once with MTBE (43 L) and twice with IPAc (2×43 L). The aqueous layer was treated with 2M hydrochloric acid (0.56 L,) and IPAc (43 L) was then added. The resulting biphasic solution was stirred and acidified with a second portion of 2M hydrochloric acid (5.04 L,). The two layers were separated and the aqueous phase (pH 3.8) was extracted with IPAc (43 L) and the combined organic extracts washed with water (21 L). The resulting solution was treated with Ecosorb™ C-941 (0.43 kg) and stirred for 1 hour at room temperature. The mixture was filtered washing the filterbed with IPAc (2×12 L). The filtrate was concentrated under reduced pressure to a total volume of ca. 20 L and the combined washes were then added along with a further portion of IPAc (16 L). The slurry was concentrated to a total volume of ca. 20 L and heptane (10 L) was added over a period of 30 minutes, at room temperature. The resulting slurry was aged, and then cooled to 0° C. The solids were then collected by filtration, washing with 2:1

IPAc:heptane (4.5 L). The off-white solid was dried under vacuum, with a slight nitrogen purge, overnight at 45° C. to afford the BOC-protected intermediate (3.45 kg; 71% overall yield from the phosphorane intermediate).

$^1$H NMR (250 MHz, CD$_2$Cl$_2$) δ 9.8-8.9 (br, 1 H), 8.43 (s, 2 H), 7.49 (d, J=7.6 Hz, 1 H), 6.97 (d, J=7.6 Hz, 1 H), 4.2-2.5 (br, 2 H), 3.93 (s, 3 H), 3.64 (app quintet, J=7.2 Hz, 1H), 2.94 (dd, J=17.4, 6.6 Hz, 1 H), 2.78 (dd, J=17.2, 9.8 Hz, 1 H), 2.71-2.61 (m, 5 H), 2.56 (dd, J=15.7, 7.6 Hz, 1 H), 2.45-2.29 (m, 2 H), 1.87-1.44 (m, 8 H), 1.35 (s, 9H); $^{13}$C NMR (63 MHz, CD$_2$Cl$_2$) δ 208.3, 173.8, 164.9, 159.2, 158.8, 154.8, 153.9, 140.0, 132.6, 130.7, 122.0, 80.3, 55.2, 47.9, 47.1, 42.8, 40.6, 36.7, 33.4, 32.2, 29.8, 29.6, 28.3, 26.3, 23.4.

EXAMPLE 12

(3S)-3-(2-Methoxypyrimidin-5-yl)-5-oxo-9-(6,7,8,9-tetrahydro-5H-pyrido[2,3-b]azepin-2-yl)nonanoic acid

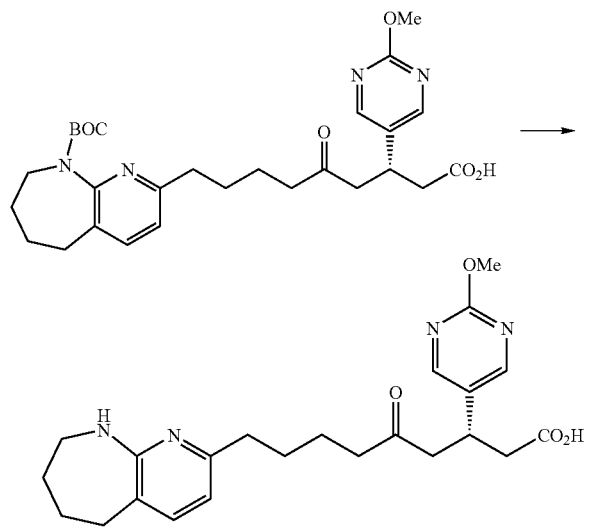

The BOC-protected product of Example 11 (15 g) was dissolved in dichloromethane (75 ml) and the solution cooled to 5° C. Trifluoroacetic acid (48.7 g) was added dropwise maintaining the internal temperature at <10° C. The reaction mixture was then heated to 30° C. and aged for ca. 2 hours. The reaction mixture was then cooled to 0° C. and a 2M solution of sodium hydroxide was added dropwise maintaining the temperature at or below ambient. The resulting solution was allowed to settle for ca. 1 hour and the layers separated. The aqueous layer was treated with Ecosorb™ C-941 (0.75 g) at ambient temperature for 1 hour. The resulting mixture was filtered through a bed of Hyflo™. The filter-bed was washed with water (10 ml). The combined filtrates were acidified to pH 6.0 by adding concentrated hydrochloric acid (ca. 8 ml) whilst maintaining the temperature at or below ambient temperature. The aqueous solution was extracted with dichloromethane (2×150 ml) and the organics washed with water (50 ml). The solution was solvent switched to isopropanol (65 ml) at atmospheric pressure and the solution warmed to 40° C., seeded with 0.6% w/w seed, and maintained at 40° C. for 12 hours. Heating was then removed and the slurry allowed to cool to 20° C. Isolation by filtration and washing with isopropanol (3×15 ml) afforded the title compound (9.0g, 74% yield).

$^1$H NMR (400 MH, DMSO-d$_6$) δ 8.34 (s, 2 H), 7.07 (d, J=7.4 Hz, 1 H), 6.31 (d, J=7.4 Hz, 1 H), 3.79 (s, 3 H), 3.41-3.32 (m, 1 H), 3.01-2.96 (m, 2 H), 2.79 (dd, J=17.1, 6.4 Hz, 1 H), 2.74 (dd, J=17.1, 7.8 Hz, 1 H), 2.58-2.20 (m, 8 H), 1.65-1.52 (m, 4 H), 1.48-1.32 (m, 4H); $^{13}$C NMR (101 MHz, DMSO-d$_6$) δ 209.3, 173.1, 165.0, 162.0, 159.3, 157.7, 139.5, 131.2, 121.7, 113.8, 55.1, 47.9, 45.6, 43.1, 40.6, 37.3, 33.6, 32.6, 30.9, 29.2, 27.1, 23.9.

EXAMPLE 13

Preparation of TRIS Salt of Compound of Formula (A) Where n=3

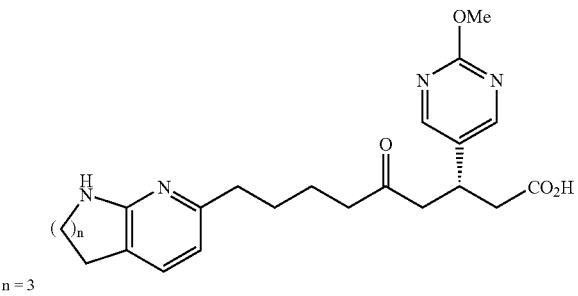

n = 3

A slurry of the zwitterion of the compound of formula (A) where n=3 (3.62 kg) and tris(hydroxymethyl)aminomethane (1.01 kg) in 2-propanol (35.7 L) and water (1.46 L) was heated to reflux to effect dissolution. The resulting solution was then cooled to 50° C. and seeded with authentic TRIS salt of the compound of formula (A) where n=3 (3.0 g). The batch was aged for 1 h at 50° C. and then cooled to 20° C. over a period of 2 h. The resulting slurry was diluted with 2-propanol (25 L) and then concentrated under a partial vacuum at 35° C., to a volume of 35 L. This procedure was repeated until the water content had reached <1.0% according to a Karl Fisher titration. Upon completion, the slurry was cooled to 20° C. and the solids filtered. The wet cake was washed with 2-propanol (1×20 L; 1×15 L) and dried overnight at 40° C. under vacuum to afford 4.40 kg of the TRIS salt (95% yield, 100 wt % pure) as a white solid.

The invention claimed is:

1. A process for the preparation of a compound of formula (I)

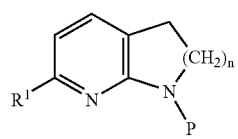

comprising closing the ring of a compound of formula (II) with heat (II)

wherein R¹ is hydrogen, chlorine, bromine or lower alkyl, P is an amino protecting group and n is 2 or 3, and Y is a group selected from chlorine, bromine, iodine, mesylate, tosylate, brosylate, nosylate or triflate.

2. A process for the preparation of a compound of formula (I)

(I)

wherein R¹ is hydrogen, chlorine, bromine or lower alkyl, P is an amino protecting group and n is 2 or 3, comprising (a) reacting a compound of formula (III)

(III)

wherein R¹ and P are as previously defined and R³ is hydrogen or methyl, with a compound of the formula (IV)

$$X—(CH_2)_m—Y \quad (IV)$$

wherein Y is a group selected from chlorine, bromine, iodine, mesylate, tosylate, brosylate, nosylate, or triflate, X is a group selected from chlorine, bromine, iodine, mesylate, tosylate, brosylate, nosylate, or triflate, and m is 3 or 4 when R³ is hydrogen, or m is 2 or 3 when R³ is methyl, to yield a compound of formula (II)

(II)

and (b) closing the ring of the compound of formula (II) with heat.

3. A process as claimed in claim 1 wherein R¹ is a chlorine atom.

4. A process as claimed in claim 3 wherein Y is a chlorine atom.

5. A process as claimed in claim 4 wherein X is a bromine or iodine atom.

6. A process as claimed in claim 5 wherein the compound of formula (IV) is selected from $Cl(CH_2)_4I$, $Cl(CH_2)_3I$, $Cl(CH_2)_2I$, $Cl(CH_2)_4Br$, $Cl(CH_2)_3Br$ and $Cl(CH_2)_2Br$.

7. A process for the preparation of the compounds of the formulae (V) and (VI):

(V)

(VI)

comprising reacting a compound of the formula (VII)

(VII)

with an alkyllithium to form a reaction mixture, and reacting the reaction mixture with the compound of the formula (IV)

$$X—(CH_2)_m—Y \quad (IV)$$

wherein Y is a group selected from chlorine, bromine, iodine, mesylate, tosylate, brosylate, nosylate, and triflate, X is a group selected from chlorine, bromine, iodine, mesylate, tosylate, brosylate, nosylate, or triflate, and m is 3 or 4, to yield a compound of the formula (VIII)

(VIII)

wherein Y is as previously defined, and p is 3 or 4, and
cyclizing the compound of formula VIII, with heat, without isolation, to form the compounds of formulae (V) and (VI).

8. A process as claimed in claim 2 wherein $R^1$ is a chlorine atom, Y is a chlorine atom, and X is a bromine or iodine atom.

9. A process as claimed in claim 8 wherein the compound of formula (IV) is selected from $Cl(CH_2)_4I$, $Cl(CH_2)_3I$, $Cl(CH_2)_2I$, $Cl(CH_2)_4Br$, $Cl(CH_2)_3Br$ and $Cl(CH_2)_2Br$.

10. A process as claimed in claim 2 wherein n is 3 and P is selected from: tert-butylmethoxyphenylsilyl, tert-butoxydiphenylsilyl, trimethylsilyl, triethylsilyl, acetyl, pivaloyl (2,2-dimethyl-1-oxopropyl), o-nitrobenzyloxycarbonyl, p-nitrobenzyloxycarbonyl, benzyloxycarbonyl, tert-butyloxycarbonyl (t-BOC), 2,2,2-trichloroethyloxycarbonyl, benzhydryl, o-nitrobenzyl, p-nitrobenzyl, 2-naphthylmethyl, benzyl, 2,2,2-trichloroethyl, tert-butyldimethylsilyl, tert-butyldiphenylsilyl, 2-(trimethylsilyl)ethyl, p-methoxybenzyl, p-methoxyphenyl, 4-pyridylmethyl, tert-butyl, allyloxycarbonyl, di-$C_{1-10}$ alkylphosphoryl, diarylphosphoryl and di-ar-$C_{1-10}$ alkylphosphoryl.

* * * * *